United States Patent
May et al.

(10) Patent No.: US 9,428,437 B2
(45) Date of Patent: Aug. 30, 2016

(54) METHOD FOR DEHYDRATING ALPHA-SUBSTITUTED CARBOXYLIC ACIDS

(71) Applicants: Alexander May, Seeheim-Jugenheim (DE); Steffen Krill, Muehltal (DE); Joerg Becker, Karlsruhe (DE); Willi Ploesser, Seeheim-Jugenheim (DE); Marcel Treskow, Darmstadt (DE); Martin Koestner, Darmstadt (DE)

(72) Inventors: Alexander May, Seeheim-Jugenheim (DE); Steffen Krill, Muehltal (DE); Joerg Becker, Karlsruhe (DE); Willi Ploesser, Seeheim-Jugenheim (DE); Marcel Treskow, Darmstadt (DE); Martin Koestner, Darmstadt (DE)

(73) Assignee: EVONIK ROEHM GmbH, Darmstadt (DE)

( * ) Notice: Subject to any disclaimer, the term of this patent is extended or adjusted under 35 U.S.C. 154(b) by 0 days.

(21) Appl. No.: 14/891,861

(22) PCT Filed: Apr. 28, 2014

(86) PCT No.: PCT/EP2014/058578
§ 371 (c)(1),
(2) Date: Nov. 17, 2015

(87) PCT Pub. No.: WO2014/191145
PCT Pub. Date: Dec. 4, 2014

(65) Prior Publication Data
US 2016/0090344 A1 Mar. 31, 2016

(30) Foreign Application Priority Data
May 27, 2013 (DE) .......................... 10 2013 209 821

(51) Int. Cl.
*C07C 51/44* (2006.01)
*C07C 51/47* (2006.01)
*C07C 51/48* (2006.01)
*C07C 51/377* (2006.01)
*C07C 51/43* (2006.01)

(52) U.S. Cl.
CPC .............. *C07C 51/377* (2013.01); *C07C 51/43* (2013.01); *C07C 51/44* (2013.01); *C07C 51/47* (2013.01); *C07C 51/48* (2013.01)

(58) Field of Classification Search
CPC ............................ C07C 51/377; C07C 51/44
See application file for complete search history.

(56) References Cited

U.S. PATENT DOCUMENTS 3,414,485 A * 12/1968 Speed .................. C07C 51/252 203/15
3,562,320 A 2/1971 Woodward et al.

FOREIGN PATENT DOCUMENTS

DE 1 768 253 10/1971
JP 57149239 A * 9/1982
WO WO 2010/071019 A1 * 6/2010

OTHER PUBLICATIONS

International Search Report issued Sep. 18, 2014, in PCT/EP2014/058578 filed Apr. 28, 2014.

* cited by examiner

*Primary Examiner* — Paul A Zucker
(74) *Attorney, Agent, or Firm* — Oblon, McClelland, Maier & Neustadt, L.L.P.

(57) ABSTRACT

The present invention describes a process for preparing alpha-beta-unsaturated carboxylic acids by dehydration of hydroxycarboxylic or alkoxycarboxylic acids which are substituted in the alpha position, in particular 2-hydroxy-isobutyric acid, while avoiding accumulation of by-products and additives.

13 Claims, 1 Drawing Sheet

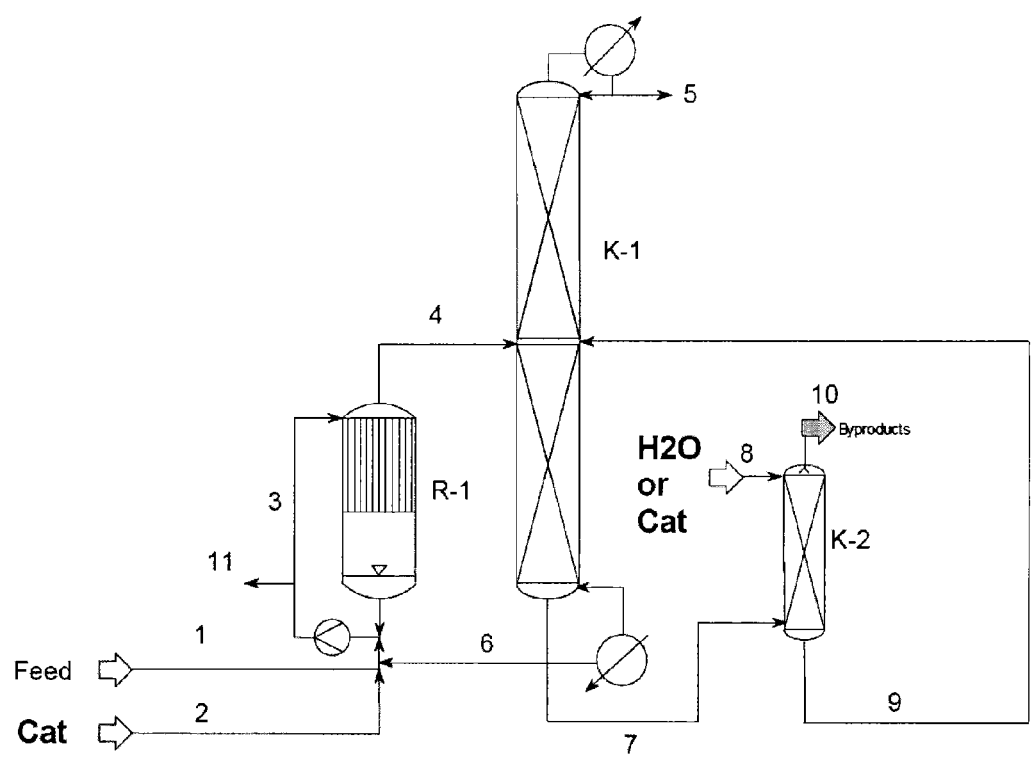

METHOD FOR DEHYDRATING ALPHA-SUBSTITUTED CARBOXYLIC ACIDS

CROSS-REFERENCE TO RELATED APPLICATIONS

The present application is a 35 U.S.C. §371 national stage patent application of International patent application PCT/EP2014/058578, filed on Apr. 28, 2014, the text of which is incorporated by reference, and claims the benefit of the filing date of German application no. 10 2013 209 821.9, filed on May 27, 2013, the text of which is also incorporated by reference.

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable.

INCORPORATION-BY-REFERENCE OF THE MATERIAL ON THE COMPACT DISC

Not Applicable.

BACKGROUND OF THE INVENTION

1. Field of the Invention

The present invention describes a process for preparing alpha-beta-unsaturated carboxylic acids by dehydration of hydroxycarboxylic or alkoxycarboxylic acids which are substituted in the alpha position, in particular 2-hydroxyisobutyric acid (2-HIBA), while avoiding accumulation of by-products and additives.

2. Description of the Related Art Including Information Disclosed Under 37 CFR 1.97 and 1.98

Such processes are adequately known from the prior art. CH 430691 describes the dehydration of 2-HIBA in methanol in the liquid phase using NaOH as catalyst to form MMA and MAS. The catalyst is added in only small amounts. To achieve the high temperature of 260° C., phthalic anhydride and tetraethylene glycol dimethyl ether are used as bath liquid.

DE1568948 discloses a dehydration of 2-HIBA dissolved in alcohol or molten 2-HIBA in the liquid phase in the presence of catalysts consisting of basic compounds which lead to formation of hydroxyisobutyrate anions and in the presence of high-boiling, polar solvents.

In a manner similar to the above, DE1211153 discloses a dehydration of 2-HIBA dissolved in alcohol or of methyl 2-hydroxyisobutyrate (M-2-HIB) in the gas phase over various fixed-bed catalysts at 250-400° C. Catalysts used are, inter alia, supported phosphates, supported sulphates, $Al_2O_3$, ZnO, $MoO_3$—$Al_2O_3$, MgO, $BPO_4$.

Catalysts disclosed in DE1768253 are alkali metal and alkaline earth metal salts of 2-HIBA (Na, K, Li, Ca, Mg, Ba, Sr) used as, for example, hydroxides, carbonates, sulphites, acetates or phosphates. The dehydration is preferably carried out at atmospheric pressure and 210-225° C. with addition of polymerization inhibitors. This disclosure also describes continuous introduction of the catalyst and partial discharge of the reactor contents in order to avoid accumulation of catalyst and by-products here. However, recovery of the target product which is necessarily likewise discharged is not described.

EP 487853 discloses a process for preparing methacrylic acid (MAA), which comprises the following steps: a) preparation of acetocyanohydrin (ACH) from acetone and HCN, b) synthesis of hydroxyisobutyramide (HIBAm) by hydrolysis of ACH over $MnO_2$, c) homogeneous catalytic conversion of HIBAm into MHIB using methyl formate or MeOH/CO with formation of formamide and d) hydrolysis of MHIB to 2-HIBA with subsequent dehydration to form MAA and $H_2O$. The last reaction step is described as continuous with introduction of stabilizers. The difficulties which inevitably result therefrom in long-term operation by accumulation of by-products, etc., are not discussed.

According to DE 1191367 the dehydration of alpha-hydroxy carboxylic acids is carried out in the presence of Cu and hydroquinone as polymerization inhibitor and also a mixture of alkali metal chlorides or bromides and corresponding halide salts of Zn, Sn, Fe, Pb as catalyst at temperatures of 185-195° C. Continuous operation and possible problems associated with recirculations are not described. The inventors' own experiments show that, firstly, the use of halide salts as catalysts result in formation of alpha-halogenated reaction by-products which have to be separated off again in a complicated manner from the actual target product, and secondly the use of halogenated compounds requires the use of appropriately resistant technical materials, which make the process more expensive, because of their corrosive action.

According to DE 102005023975 the dehydration is carried out in the presence of at least one metal salt, for example alkali metal and/or alkaline earth metal salts, at temperatures of 160-300° C., particularly preferably from 200 to 240° C. Metal salts mentioned there as being suitable include, inter alia, sodium hydroxide, potassium hydroxide, calcium hydroxide, barium hydroxide, magnesium hydroxide, sodium sulphite, sodium carbonate, potassium carbonate, strontium carbonate, magnesium carbonate, sodium bicarbonate, sodium acetate, potassium acetate and sodium dihydrogen phosphate. A particular aspect is that the pressure of the dehydration stage is the same as that in a preceding transesterification stage and is preferably in the range 0.1-1 bar. Discharge of by-products is not disclosed.

It is common to these processes described in the prior art, in particular those configured as a continuous variant, that polymerization inhibitors have to be added to the reactor feed or the reaction mixture introduced into the distillation column which generally follows the reactor in order to avoid polymerization of the target products. Without further measures for removal or discharging, the substances continually accumulate in the reactor, associated with corresponding disadvantages such as deposit formation or discolouration.

Furthermore, the reaction of the alpha-substituted carboxylic acids is never complete. The recirculation of unreacted reactants is therefore absolutely necessary in order to achieve an economical industrial process. The documents cited in the prior art discuss neither such a necessary product recirculation nor the formation and elimination of by-products. In addition, regardless of the catalyst used in the reaction of, for example, alpha-hydroxy carboxylic acids, by-products typical for this reaction are always formed at least in traces even in the case of very good selectivities of >98%. All these by-products have a boiling point similar to that of the alpha-substituted carboxylic acids and thus inevitably accumulate in the recirculation of the unreacted starting materials. The same applies to polymerization inhibitors which are added to the reaction and have boiling points similar to that of the starting material.

Thus, if no further technical measures are undertaken, the secondary components or additives described accumulate continuously in the recirculation of starting material, which firstly leads to an overall increase in the recycle stream and increases the energy consumption in the respective revaporization in the reactor circuit. To avoid this continuous accumulation of undesirable by-products, a discharge measure by means of which a constant by-product or additive level can be realized in the reaction system is therefore necessary. However, from an economic point of view undifferentiated discharge is disadvantageous since target product and catalyst are also lost alongside the undesirable by-products and excess polymerization inhibitors.

Although the publication "Avoiding Accumulation of Trace Components" (Ind. Eng. Chem. Res. 1992, 31, 1502-1509) discusses, in numerous variants, the possible discharge of by-products which occur in traces, there is no discussion of recirculation of any concomitantly discharged target products downstream of the discharge point.

It is therefore an object of the present invention to avoid accumulation of undesirable by-products and additives, in particular excess polymerization inhibitors, by discharging these from the reaction process in order to achieve a stable concentration equilibrium and at the same time to minimize the loss of target product and to optimize the energy consumption for maintaining the circulation streams. Further objects which are not explicitly mentioned can be derived from the overall contents of the following description, claims and examples.

BRIEF SUMMARY OF THE INVENTION

The abovementioned object is achieved by a process for dehydrating alpha-substituted carboxylic acids, characterized in that at least part of the reaction stream is continuously discharged from the reaction circuit, by-products or excess additives are separated off from the unreacted starting material and the latter is reintroduced into the reaction circuit.

Suitable starting materials for this process are alpha-substituted carboxylic acids of the formula (1):

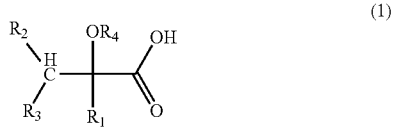

where $R_1$=H or CHR'R"; $R_2$ and $R_3$ are each, independently of one another, H or a carbon radical having 1-7 carbon atoms, linear, branched or alicyclic; $R_4$=H or a carbon radical having 1-3 carbon atoms, linear or branched; R' and R" are each, independently of one another, H or a carbon radical having 1-3 carbon atoms.

The excess additives to be discharged are essentially polymerization inhibitors which are intended to prevent polymerization of the alpha-beta-unsaturated carboxylic acids formed as target products. Suitable initiators are, for example, hydroquinones, hydroquinone ethers, such as hydroquinone monomethyl ether or di-tert-butylcatechol, phenothiazine, 4-hydroxy-2,2,6,6-tetramethylpiperidin-1-oxyl, N,N'-diphenyl-p-phenylenediamine, methylene blue or sterically hindered phenols (e.g. Topanol A), which are widely known to those skilled in the art. These compounds can be used individually or in the form of mixtures and are generally commercially available. The mode of action of the stabilizers is usually that they act as free-radical scavengers for the free radicals occurring in the undesirable polymerization.

For further details and alternatives, reference may be made to the relevant specialist literature, in particular Römpp-Lexikon Chemie; editor: J. Falbe, M. Regitz; Stuttgart, New York; 10th edition (1996); keyword "Antioxidantien", and the literature references cited there. Preference is given to using, in particular, phenols as polymerization inhibitors. Particular advantages can be achieved when using hydroquinone monomethyl ether. Based on the weight of the total reaction mixture, the proportion of inhibitors individually or as a mixture can generally be 0.01-0.5% by weight and is kept in this range by means of an appropriate introduction and discharge equilibrium.

By-products typical of the dehydration reaction are, for example, dimeric or oligomeric forms of the alpha-substituted hydroxycarboxylic acids, open-chain or as a cyclic compound, and also decarboxylation products of two dimeric alpha-beta-unsaturated carboxylic acids, essentially pentenoic (formula (2)) or hexenoic acids (formula (3)):

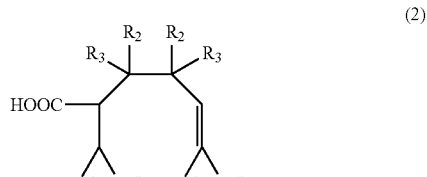

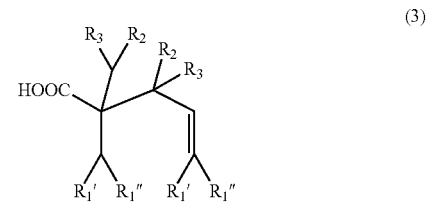

where all R substituents are, independently of one another, H or carbon chains having 1-3 carbon atoms.

The former can be redissociated into the starting materials by means of suitable process conditions, while the latter have to be discharged continually from the process.

BRIEF DESCRIPTION OF THE SEVERAL VIEWS OF THE DRAWINGS

FIG. 1: A process for dehydrating alpha-substituted carboxylic acids in which an alpha-substituted carboxylic acid is fed via line 1 in parallel with a catalyst via line 2 through circuit 3 via a heat exchanger apparatus R-1. Outflow from the reactor is fed directly in gaseous form via line 4 to a distillation column K-1, while the target product alpha-beta-unsaturated carboxylic acid is separated off as overhead product via line 5. Unreacted hydroxycarboxylic acid is fed back to the reaction via line 6.

DETAILED DESCRIPTION OF THE INVENTION

A preferred embodiment of the invention is shown in FIG. 1. The feed, viz. the alpha-substituted hydroxycarboxylic acid, is fed as melt, aqueous or alcoholic solution via line 1 into the reactor circuit R-1. In parallel, the catalyst can be introduced continuously or at intervals via line 2. The catalyst can be present as a solution in starting material, product or water. The starting material and the catalyst are conveyed through the circuit 3 via a heat exchanger apparatus R-1 which can be, for example, a falling film heat exchanger, shell-and-tube heat exchanger with or without internals in the tubes in order to increase the turbulence, as are commercially available, for example, from Calgavin, or a plate heat exchanger. The energy necessary for the reaction and for vaporization of the reaction products is introduced at the heat exchanger. The outflow from the reactor is fed directly in gaseous form via line 4 to a distillation column K-1 in which water and also the target product alpha-beta-unsaturated carboxylic acid are separated off as overhead product via line 5. At the bottom of the column, the unreacted hydroxycarboxylic acid is fed back as substream to the reaction via line 6. Polymerization inhibitors which have been introduced into the feed and/or the column K-1 and also secondary components which have left the reactor R-1 in gaseous form but go into the bottoms together with the hydroxycarboxylic acid in the column K-2 are likewise recycled via line 6.

Without further technical measures, both these polymerization inhibitors and the abovementioned by-products accumulate in the reactor circuit, which leads to a volume increase of the circulation stream 6 itself and, on renewed vaporization of the reaction mixture in reactor R-1, increases the energy consumption. To avoid these disadvantages, a substream of the circulation stream 6 is taken off via a discharge line 7 and fed to a scrubbing stage K-2 to which water or a substream of the aqueous catalyst solution is fed as scrubbing liquid 8. Possible apparatus designs for the scrubbing stage K-2 can be: mixer-settler units (single-stage or multistage, preferably single-stage); static, pulsed or stirred extraction columns. Typical internals here are random packing elements, sieve trays (static or pulsed design) and also static packings. These apparatus designs are known to those skilled in the art and are described, inter alia, in K. Sattler, Thermische Trennverfahren, Wiley-VCH, 2001. The hydroxycarboxylic acid present in stream 7 here preferably goes into the aqueous phase which goes via line 9 back to column K-1. The loss of target product is minimized in this way. The polymerization inhibitors and by-products which are insoluble in water form a separate organic phase in the scrubber K-2 and can in this way be discharged from the process selectively and without target product via an outlet 10.

Should high-boiling by-products which cannot go via the gas phase of stream 4 to the bottom of the distillation column K-1 accumulate in the reactor circuit 3, it is possible to eliminate these directly from the reactor circuit by means of a substream via line 11. The discharge stream 11 then contains essentially catalyst and hydroxycarboxylic acid as components to be recovered and can for this purpose likewise be fed to the scrubber K-2.

The phase separation induced the scrubbing column K-2 by introduction of water or aqueous catalyst solution surprisingly proceeds particularly well when the concentration of by-products and/or polymerization inhibitors in the discharge stream 7 exceeds a particular value. It is therefore advantageous to branch off the discharge stream 7 only after an induction period, when this limit concentration has been reached. In the case of the conversion of 2-HIBA into MAA, this means a concentration of 10-30% by weight, preferably 15-25% by weight, particularly preferably 17-22% by weight, of 2-methylhexen-4-oic acid (2-MHA) at the bottom of column K-1.

The process water obtained in the reaction can also be used instead of fresh water to induce the phase separation in the scrubbing column K-2. This avoids an increased wastewater stream. However, introduction of a substream of the aqueous catalyst solution is particularly advantageous: the catalyst which is in any case present in solution remains in the aqueous phase which is recycled, and the catalyst is therefore not lost, improves the solubility of the starting materials to be recovered and increases the density of the aqueous phase, which favours good and rapid phase separation. The mass ratios of water or aqueous catalyst solution to discharge stream 7 are 0.5:1-5:1, preferably 1:1-3:1 and particularly preferably 1.1:1-1.5:1. The phase separation is carried out at temperatures of 0-60° C., preferably at 5-40° C. and particularly preferably at 10-35° C.

It has been found that the amount of material of value from the process can be increased when the reaction mixture of water and discharged reaction stream is heated to at least 70° C., preferably to at least 90° C., for at least 2 minutes, preferably at least 5 minutes, particularly preferably at least 10 minutes, before the phase separation. As a result of the heating, the hydrophobic tetramethyl glycolide present in the reaction stream is converted into the more hydrophilic 1-carboxy-1-methylethyl 2-hydroxyisobutyrate. Thus, the more hydrophilic 1-methylethyl 2-hydroxyisobutyrate remains predominantly in the aqueous phase and can be recirculated to the process.

The aqueous target product solution can be recirculated either into the reactor R-1 or into the distillation column K-1. Recirculation into the latter is preferred.

To separate off by-products and additives from the starting material after the discharge point, it is also possible to employ other separation processes such as distillation, crystallization or adsorption. These processes are described in customary textbooks of process engineering, e.g. Stichlmair, J. 2010. Distillation, 3. Processes, Ullmann's Encyclopedia of Industrial Chemistry, Published Online: Apr. 15, 2010; Mullin, J. W. 2003, Crystallization and Precipitation, Ullmann's Encyclopedia of Industrial Chemistry, Published Online: Jan. 15, 2003 or Bart, H.-J. and von Gemmingen, U. 2005, Adsorption, Ullmann's Encyclopedia of Industrial Chemistry. Published Online: Jan. 15, 2005. In these alternative separation processes, adherence to an induction period is generally not necessary, but carrying them out requires a greater outlay in terms of apparatus and energy.

The dehydration reaction itself can occur in CSTRs or loop reactors, with the target product being removed from the reaction mixture by distillation on the basis of the boiling point which is lower than that of the starting material. The reaction is carried out at pressures of 0.01-1 bar, preferably 0.05-0.5 bar, particularly preferably 0.1-0.3 bar and temperatures of 30-300° C., preferably 80-250° C., particularly preferably 180-230° C.

Suitable catalysts are, for example, the compounds cited in the prior art; preference is given to using alkali metal hydroxides. It is advantageous to use 0.1-5 mol, preferably 0.3-3 mol and particularly preferably 0.5-1.5 mol of catalyst per molar equivalent of alpha-substituted carboxylic acids fed per hour into the reactor.

The following examples illustrate the invention but do not restrict it in any way.

Comparative Example 1

32.4 kg of a melt consisting of 83.6% by weight of 2-HIBA, 12% by weight of tetramethylglycolide, 3.9% by weight of 1-carboxy-1-methylethyl 2-hydroxyisobutyrate and 0.5% by weight of 2-methoxyisobutyric acid are placed in a reactor. The melt is stabilized by 1000 ppm of hydroquinone monomethyl ether (HQME) and 1000 ppm of 2,4-dimethyl-6-tert-butylphenol (Topanol A). 13.75 kg of 85% strength KOH are added to the melt in the reactor, with the contents of the reactor being maintained at about 150° C. during addition of the catalyst. After addition of the catalyst, the contents of the reactor are heated to 215° C. by pumping through a falling film heat exchanger and a reduced pressure of 150 mbar is applied. The falling film heat exchanger is heated on the shell side by means of a heat transfer oil (Marlotherm SH). Turbulators from Calgavin are installed in the tubes of the falling film heat exchanger to improve heat transfer. In steady-state operation, the heat transfer oil is heated to 225° C. in order to achieve the reaction temperature. A feed stream of 11.2 kg/h having the above composition is then fed to the reactor. The vapour stream leaving the reactor is conveyed into the downstream column which is at a reduced pressure of 80 mbar.

The reaction products MAA and water are taken off as overhead product. To achieve a better separation performance, 20 kg/h of the distillate obtained are reintroduced as runback into the column. In addition, the condenser is sprayed with 200 ml/h of a methanolic solution of 10% by weight of HQME and 5% by weight of Topanol A in order to avoid polymerization. Unreacted products, polymerization inhibitors and high-boiling by-products are separated off at the bottom of the column and fed back to the reactor. The distillate stream obtained from the column was 11.4 kg/h. A small part of the overhead product goes uncondensed into the vacuum system. To avoid accumulation of polymeric by-products in the reactor, a stream of 200 g/h is continuously discharged from the reactor 12 hours after commencement of the reaction. To replace the loss of potassium, 300 g/h of KOH are introduced as 17% strength solution in $H_2O$. The reaction is operated over a period of four weeks. After four weeks, the experiment was stopped since the recycle stream from the bottom of the column to the reactor had increased greatly.

The feed stream, the distillate from the column and the recycle stream from the column were sampled and analysed at regular intervals. 2-HIBA, tetramethylglycolide, 1-carboxy-1-methylethyl 2-hydroxyisobutyrate and methacrylic acid are measured by means of HPLC, while all the other components $H_2O$, methanol, 2-methoxyisobutyric acid and also HQME and Topanol A are analysed by GC. The components 2-HIBA, tetramethylglycolide and 1-carboxy-1-methylethyl 2-hydroxyisobutyrate are summarized in the collective parameter w_HIBA_eq as molar equivalents of 2-HIBA. The distillate obtained during the reaction consisted on average of 19.0% by weight of $H_2O$, 80.4% by weight of methacrylic acid and also 0.2% by weight of 2-methoxyisobutyric acid and 0.4% by weight of methanol.

A degree of conversion per pass through the reactor of w_HIBS_eq=67% at a selectivity to methacrylic acid of 97.4% is achieved in the reaction. By-products formed are predominantly cis- and trans-2-methylhexen-4-oic acid (2-MHA).

The analytical results of the recycle stream from the bottom of the column back to the reactor for the operating times of 100, 250, 390 and 650 h are summarized in % by weight in Tab. 1.

TABLE 1

Analysis of the recycle stream

| Component in the bottoms from the column % by weight | 100 h Bottoms A | 250 h Bottoms B | 390 h Bottoms C | 650 h Bottoms D |
|---|---|---|---|---|
| 2-HIBA | 74.0 | 63.1 | 58.3 | 34.4 |
| Tetramethylglycolide | 13.0 | 9.1 | 4.3 | 4.0 |
| 1-carboxy-1-methylethyl 2-hydroxyisobutyrate | 0.75 | 0.6 | 0.5 | 0.2 |
| 2-methoxyisobutyric acid | 0.5 | 0.5 | 0.5 | 0.4 |
| 2-MHA | 8.0 | 19.0 | 27.4 | 50.9 |
| Σ (HQME + Topanol A) | 1.6 | 3.5 | 3.9 | 6.3 |
| Phase separation using water | No | Yes | Yes | Yes |
| Phase separation using KOH | No | Yes | Yes | Yes |

The results confirm that 2-methoxyisobutyric acid reacts fully since no accumulation effect is observed. The total degree of conversion of 2-methoxyisobutyric acid over the total process unit reaches 60%. Dimeric compounds of 2-HIBA (1-carboxy-1-methylethyl 2-hydroxyisobutyrate and tetramethylglycolide) also do not accumulate but react fully. Owing to the high selectivity to methacrylic acid achieved, it has to be assumed that these compounds, too, react at least mostly to form methacrylic acid. By-products such as 2-MHA and also the polymerization inhibitors, on the other hand, accumulate continually over the operating time without reaching a steady-state level. Furthermore, it can be seen phase separation of samples taken from the various bottoms from the columns can be induced only above a particular concentration of by-products. The composition of the phases is shown by way of example for bottoms B in Tab. 2.

TABLE 2

Proportions by mass of the two phases and composition in % by weight

| | Bottoms B plus water | | Bottoms B plus KOH | |
|---|---|---|---|---|
| Component in the bottoms from the column | Aqueous phase | Organic phase | Aqueous phase | Organic phase |
| Proportion by mass in % | 83 | 17 | 89 | 11 |
| Of which | | | | |
| $H_2O$ | 73 | 36 | 52 | 32 |
| Potassium as KOH | — | — | 9.4 | 5.7 |
| w_HIBA_eq | 25 | 20 | 37 | 21 |
| 2-MHA | 1.7 | 30 | 6.3 | 28 |
| Σ (HQME + Topanol A) | 0.1 | 6.5 | 0.7 | 8.6 |

Example 1

As Example 1 according to the invention, Comparative Example 1 was essentially repeated with the following changes being made in the experimental arrangement and procedure: a small substream of 0.4 kg/h is taken from the recycled stream from the bottom of the column when a total concentration of 20% by weight of 2-MHA and of the inhibitors HQME and Topanol A was exceeded, here after an operating time of 200 h. This substream is mixed with 0.5 kg/h of water and fed to a residence vessel maintained at 15° C. for phase separation. The aqueous phase is recirculated to the middle of the column downstream of the reactor. The organic phase is discharged and discarded. The inflow of polymerization inhibitor solution was 300 ml/h. The experiment is operated over a period of six weeks. The distillate stream obtained from the column was 11.9 kg/h. The distillate obtained during the reaction consisted on average of 22.0% by weight of H$_2$O, 77.0% by weight of methacrylic acid and also 0.1% by weight of 2-methoxyisobutyric acid and 0.9% by weight of methanol.

A degree of conversion per pass through the reactor of w_HIBA_eq=64% at a selectivity to methacrylic acid of 97.1% is achieved in the reaction. By-products formed are mainly 2-MHA.

The analytical results for the recycle stream from the bottom of the column back to the reactor for the operating times of 190, 360, 700 and 950 h are as summarized in % by weight in Tab. 3.

TABLE 3

Analyses of the recycle stream

| Component in the bottoms from the column (% by weight) | 190 h | 360 h | 700 h | 950 h |
|---|---|---|---|---|
| 2-HIBA | 65 | 55 | 55 | 55 |
| Tetramethylglycolide | 11 | 9.5 | 9.0 | 8.5 |
| 1-carboxy-1-methylethyl 2-hydroxyisobutyrate | 0.7 | 0.5 | 0.6 | 0.8 |
| 2-methoxyisobutyric acid | 0.6 | 0.7 | 0.6 | 0.6 |
| 2-MHA | 15.0 | 21.6 | 20.4 | 21.2 |
| Σ (HQME + Topanol A) | 4.5 | 6.5 | 6.8 | 7.7 |

The average analytical results for the aqueous and organic phases obtained in the phase separator are summarized for the operating period 200-1000 h in Tab. 4.

TABLE 4

Proportions by mass of the two phases and composition in % by weight

| Component in the bottoms from the column | Example 1 aqueous phase | Example 1 organic phase |
|---|---|---|
| Proportion by mass in % Of which | 82 | 18 |
| H$_2$O | 61.4 | 35.5 |
| w_HIBA_eq | 30.4 | 24.3 |
| 2-MHA | 6.0 | 29.3 |
| 2-methoxyisobutyric acid | 0.7 | 1.0 |
| Σ (HQME + Topanol A) | 1.5 | 9.9 |

Example 2

Example 1 according to the invention was essentially repeated with the following changes being made in the experimental arrangement and procedure:

The falling film evaporator was replaced by a plate heat exchanger. In contrast to the falling film evaporator, it is ensured that the plate heat exchanger is filled with liquid by setting a gauge pressure of 3 bara by means of a pressure regulating valve. A temperature of 215° C. is set downstream of the plate heat exchanger. Downstream of the pressure regulating valve, the circulating stream is depressurized to 150 mbara.

The inflow of polymerization inhibitor solution to the column was 300 ml/h. The experiment is operated over a period of 45 days. The distillate stream obtained from the column was 11.8 kg/h. The distillate obtained during the reaction consisted on average of 22.5% by weight of H$_2$O, 77.3% by weight of methacrylic acid, 0.5% by weight of tetramethylglycolide and also 0.1% by weight of 2-methoxyisobutyric acid and 0.9% by weight of methanol.

A degree of conversion per pass through the reactor of w_HIBA_eq=65.5% at a selectivity to methacrylic acid of 97.8% is achieved in the reaction. By-products formed are mainly 2-MHA.

The analytical results for the recycle stream from the bottom of the column back to the reactor for the operating times of 950 and 1090 h are summarized in % by weight in Tab. 5.

TABLE 5

Analyses of the recycle stream in Example 2 in % by weight

| Component in the bottoms from the column | 950 h | 1090 h |
|---|---|---|
| 2-HIBA | 45.0 | 49.0 |
| Tetramethylglycolide | 19.4 | 20.5 |
| 1-carboxy-1-methylethyl 2-hydroxyisobutyrate | 0.6 | 1.0 |
| 2-methoxyisobutyric acid | | |
| 2-MHA | 17.6 | 13.5 |
| Σ (HQME + Topanol A) | 4.6 | 4.2 |

The average analytical results for the aqueous and organic phases obtained in the phase separator are summarized for the operating period 950-1090 h in Tab. 6.

TABLE 6

Proportions by mass and composition of the two phases in % by weight

| Component in the bottoms from the column | Example 2 aqueous phase | Example 2 organic phase |
|---|---|---|
| Proportion by mass in % of which | 76 | 22 |
| H$_2$O | 63.3 | 22.6 |
| w_HIBA_eq | 30.3 | 31.5 |
| 2-MHA | 5.1 | 37.4 |
| 2-methoxyisobutyric acid | 0.4 | 0.3 |
| Σ (HQME + Topanol A) | 0.6 | 8.3 |

Examples 1 and 2 according to the invention show that taking off a substream of the recirculation stream of bottoms and extractive treatment of the discharged substream with water and subsequent recirculation of the starting material-containing aqueous phase makes long-term stable operation of MAA production from 2-HIBA possible and allows by-products and also polymerization inhibitors to be removed in a targeted manner and selectively from the process.

Example 3

Example 1 according to the invention was essentially repeated, with the following changes in the experimental arrangement and procedure being made:

The water stream used for extraction of the MHA was set to 0.6 kg/h. The discharge stream from the bottom of the column of 0.4 kg/h and the water stream for the extraction are mixed and are heated for 10 minutes to 90° C. in a heated tube before introduction into the residence vessel for phase separation. The stream is subsequently cooled to 40° C.; the temperature in the phase separator is likewise 40° C.

The average analytical results for the aqueous and organic phases from the phase separator for the operating period after about 900 h are summarized in Tab. 7.

TABLE 7

Proportions by mass and composition
of the two phases in % by weight

| Component in the column bottom | Example 3 aqueous phase | Example 3 organic phase |
|---|---|---|
| Proportion by mass in % | 77 | 23 |
| of which | | |
| $H_2O$ | 68.0 | 39.0 |
| w_HIBA_eq | 30.5 | 14.2 |
| 2-MHA | 0.5 | 37.9 |
| 2-Methoxyisobutyric acid | 0.3 | 0.6 |
| Σ (HQME + Topanol A) | 0.5 | 8.1 |

The brief heating of the discharge stream mixed with water enables the proportion of material of value (w_HIBA_eq) in the discharged organic phase and thus the loss of material of value to be significantly reduced further.

Experimental Conditions

1. HPLC

| Component | Name |
|---|---|
| Pump | Dionex HPLC Pump 680 |
| Column oven | Thermostated column compartment TCC-100 |
| UV detector | Ultimate 3000 Variable wavelength detector |
| HPLC column | Zorbax SB-Aq Rapid Solution 4.6 × 150 mm; 3.5 μm |
| Eluant | Acetonitrile LiChrosolv (from Merck) |
| | Potassium dihydrogen phosphate solution (0.02 mol/l) |

Temperature 55° C.

2. GC

| Component | Name |
|---|---|
| GC instrument | CP-3800 Gas chromatograph |
| Injector | 1079 PTV |
| Column | AT-WAX (Alltech); length: 30 m; ID: 0.53 mm; film: 1.2 μm |
| Detector | TCD |
| Carrier gas | Helium |

Temperature program: 40° C. to 240° C. at a rate of 20 K/min

The invention claimed is:

1. A process, comprising:
feeding a reaction stream comprising an alpha-substituted carboxylic acid into a reaction circuit,
feeding a catalyst stream comprising a catalyst into the reaction circuit,
dehydrating the alpha-substituted carboxylic acid in the reaction circuit in the presence of a polymerization inhibitor, to obtain a product stream comprising water, an alpha-beta-unsaturated carboxylic acid, unreacted alpha-substituted carboxylic acid, and the polymerization inhibitor, wherein at least part of the product stream is continuously discharged from the reaction circuit,
separating the polymerization inhibitor and the alpha-beta-unsaturated carboxylic acid from the unreacted alpha-substituted carboxylic acid, and reintroducing the unreacted alpha-substituted carboxylic acid into the reaction circuit.

2. The process of claim 1, wherein the alpha-beta-unsaturated carboxylic acid is separated off from the unreacted alpha-substituted carboxylic acid by phase separation.

3. The process of claim 2, wherein the phase separation is induced with water or an aqueous catalyst solution.

4. The process of claim 3, wherein water from the product stream is used to induce the phase separation.

5. The process of claim 3, wherein the phase separation is carried out at 0-60° C.

6. The process of claim 5, wherein the product stream is heated for at least 2 minutes to at least 70° C. before the phase separation.

7. The process of claim 1, wherein the alpha-beta-unsaturated carboxylic acid is separated off from the unreacted alpha-substituted carboxylic acid by distillation.

8. The process of claim 1, wherein the alpha-beta-unsaturated carboxylic acid is separated off from the unreacted alpha-substituted carboxylic acid by crystallization.

9. The process of claim 1, wherein the alpha-beta-unsaturated carboxylic acid is separated off from the unreacted alpha-substituted carboxylic acid by adsorption.

10. The process of claim 1, wherein unreacted alpha-substituted carboxylic acid is further recirculated to a distillation column in which the alpha-beta-unsaturated carboxylic acid is taken off at the top.

11. The process of claim 1, wherein the product stream is discharged from a bottom of a distillation column in which the alpha-beta-unsaturated carboxylic acid is taken off at the top.

12. The process of claim 1, wherein the product steam is discharged only after an induction period.

13. The process of claim 1, wherein the alpha-substituted carboxylic acid is 2-hydroxyisobutyric acid.

* * * * *